United States Patent
Sutoh et al.

(10) Patent No.: US 8,506,576 B2
(45) Date of Patent: Aug. 13, 2013

(54) GRIPPING TOOL

(75) Inventors: Dai Sutoh, Fukuroi (JP); Nobuatsu Kanie, Fukuroi (JP)

(73) Assignee: Covidien LP, Mansfield, MA (US)

( * ) Notice: Subject to any disclaimer, the term of this patent is extended or adjusted under 35 U.S.C. 154(b) by 970 days.

(21) Appl. No.: 11/622,825

(22) Filed: Jan. 12, 2007

(65) Prior Publication Data

US 2007/0167956 A1 Jul. 19, 2007

(30) Foreign Application Priority Data

Jan. 16, 2006 (JP) .................................... 2006-7828

(51) Int. Cl.
*A61F 11/00* (2006.01)

(52) U.S. Cl.
USPC .......................................................... 606/108

(58) Field of Classification Search
USPC ................. 606/108, 109; 604/93.01, 103.08, 604/164.01, 164.06, 164.11, 164.13, 540, 604/541, 544, 313, 21, 171
See application file for complete search history.

(56) References Cited

U.S. PATENT DOCUMENTS

| 3,589,368 | A |   | 6/1971 | Jackson et al. |
| 4,842,589 | A |   | 6/1989 | Fecht et al. |
| 5,325,868 | A |   | 7/1994 | Kimmelstiel |
| 6,134,467 | A | * | 10/2000 | Ouchi .............................. 604/21 |
| 6,162,221 | A | * | 12/2000 | Ouchi .............................. 606/49 |
| 6,673,060 | B1 | * | 1/2004 | Fleming, III .................. 604/540 |
| 6,964,675 | B2 | * | 11/2005 | Zhu et al. ...................... 606/213 |
| 7,022,110 | B2 | * | 4/2006 | Shibata ......................... 604/158 |
| 7,137,962 | B2 | * | 11/2006 | Gittings et al. ................... 604/8 |
| 2004/0260206 | A1 | * | 12/2004 | Murayama et al. ........... 600/585 |
| 2005/0101836 | A1 |   | 5/2005 | Onuki et al. |

FOREIGN PATENT DOCUMENTS

| JP | 2-77054 | 6/1990 |
| JP | 07051359 A | 2/1995 |
| JP | 08-000735 | 1/1996 |
| JP | 11192206 A | 7/1999 |
| JP | 2001-161805 | 6/2001 |
| JP | 2001340468 A | 12/2001 |

OTHER PUBLICATIONS

Extended European Search Report for Application No. 07000118.5-1526 dated May 11, 2007.

* cited by examiner

*Primary Examiner* — Ryan Severson
*Assistant Examiner* — David Eastwood
(74) *Attorney, Agent, or Firm* — Lisa E. Winsor, Esq.

(57) ABSTRACT

An insert (100) for a patient fluid discharge tube (A) facilitates removal of the discharge tube from the patient, wherein the insert provides a smooth outer surface (12a) and also an arrangement (20) for aiding in attaching a removal tool to the insert such that the end of the discharge tube may be easily grasped and pulled from the patient.

16 Claims, 5 Drawing Sheets

GRIPPING TOOL

FIELD OF THE INVENTION

The present invention generally relates to a gripping tool for attachment to one end of a flexible drainage tube used for discharging fluids in the body and a discharge tube for at least partial insertion into a patient's body.

BACKGROUND OF THE INVENTION

In a surgical operation, a drainage tube for draining fluids in the thoracic cavity or abdominal cavity is often used. In the method for retaining the drainage tube using the example of a thoracic cavity drainage tube, first, one end of the drainage tube is inserted into the body from an incised portion in the thoracic cavity during the surgery, for example. A loculus that connects to the thoracic cavity is also formed from the portion of the body surface positioned near the aforementioned incised portion. Then a removal member, e.g., forceps, is slipped into the thoracic cavity through the aforementioned loculus, and one end of the drainage tube is gripped.

Then the removal member is pulled out leaving the other end of the drainage tube in the thoracic cavity. By so doing, one end of the drainage tube leads out of the body, and the other end of the drainage tube is left in the thoracic cavity. In this state, a suction bag or the like is connected to the one end of the drainage tube, and by applying negative pressure to the one end of the drainage tube relative to the other end, pus, blood, or other exudates are discharged through the discharge tube outside the body (suction bag).

In the aforementioned discharge tube retention method, a forceps is generally used as the removal member, and when the end of the discharge tube is pulled out of the body by the forceps, the forceps sometimes cannot satisfactorily grip the discharge tube. For this reason, shaping the end portion of the discharge tube by cutting it on a slant to make it easy to grip with the forceps or attaching a gripping tool to the end of the discharge tube to facilitate gripping of the discharge tube have been proposed.

In addition, in Japanese Kokai Utility Model No. 2[1990] 77054 a method is proposed wherein an advance part is attached to one end of the discharge tube, a guide wire is passed inside the advance part, and the end of the discharge tube is guided outside the body by guiding the discharge tube along the guide wire.

The loculus formed in the body for slipping the removal member into the body when the end of the discharge tube is pulled out with a removal member such as forceps should preferably be a small as possible in order to reduce the burden on the patient. Therefore, when the removal member gripping an end of the discharge tube is pulled out of the body, it must be pulled so that the discharge tube follows in a direction parallel to the direction that the removal member is pulled out in order for the sectional area through which the discharge tube passes when passing through the loculus to be smaller. However, with existing removal technology, the discharge tube is not necessarily limited to being gripped following the direction that the removal member is pulled out and is often gripped at an angle to the direction that the removal member is pulled out. With such a gripping state, because the discharge tube is pointed at an angle relative to the direction the removal member is pulled out, the discharge tube sometimes interferes, and the discharge tube cannot be pulled out of a loculus that has a small surface area.

SUMMARY OF THE INVENTION

In one aspect of the present invention, a gripping tool for attachment to one end of a flexible drainage tube used for discharging fluids in the body is arranged to be gripped with a removal member for pulling the end of the drainage tube remaining in a patient's body out of the body. The gripping tool generally comprises a main body for attachment to one end of the drainage tube and a gripping part that is to be gripped by the removal member. The gripping tool also comprises a connecting part that can bend and which connects the main body and the gripping part.

In another aspect, a discharge tube for at least partial insertion into a patient's body generally comprises an end intended to be removed from the body. The end of the discharge tube includes a main body inserted therein. The main body has a first end region inserted in the discharge tube end and a second end region protruding from the discharge tube end. A through channel connects the first and second end regions and a gripping element is disposed within the through channel. The gripping element has a first end part protruding from the through channel away from the first end region including surface gripping protrusions to be gripped by a removal tool in a removal operation. The gripping element also has a second end part protruding from the through channel away from the second end region and including a stop for preventing pull-through of the gripping element through the through channel.

Other features will be in part apparent and in part pointed out hereinafter.

BRIEF DESCRIPTION OF THE DRAWINGS

The invention will now be described, by way of example only, with reference to the accompanying drawings in which:

FIGS. 7(*a*)-(*e*) are figures showing the operation when the discharge tube is pulled out with forceps in the embodiment of the present invention;

FIGS. 9(*a*) and 9(*b*) are side views showing other examples of the gripped part and the connecting part in the embodiments of the present invention.

Corresponding reference characters indicate corresponding parts throughout the drawings.

DETAILED DESCRIPTION OF THE DRAWINGS

Figure 1:
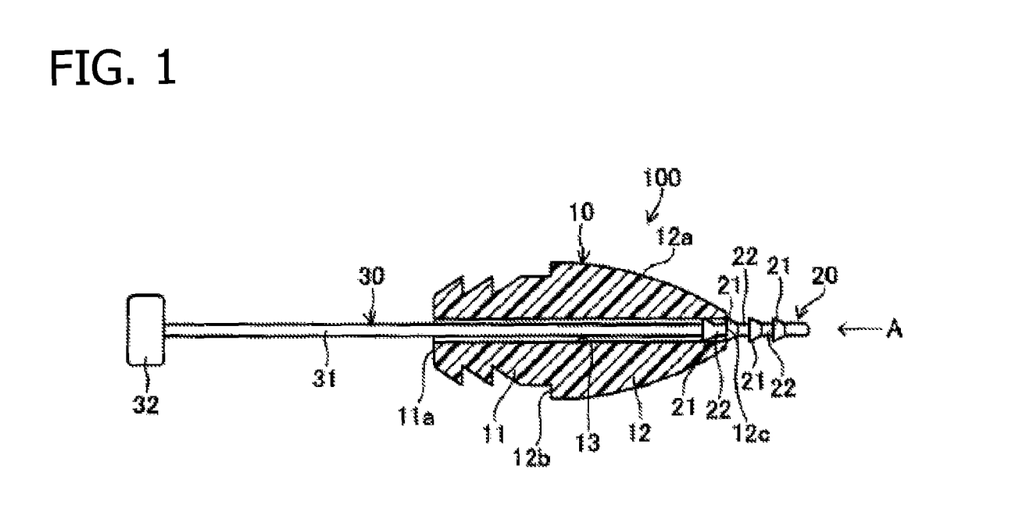
FIG. 1 is a side view of a gripping tool pertaining to an embodiment of the present invention.
Figure 2:
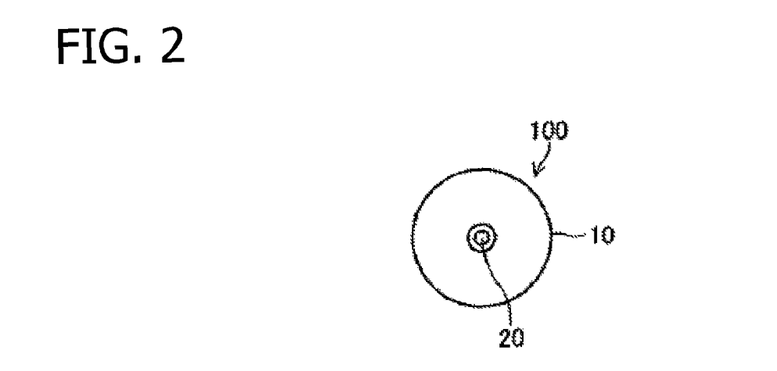
FIG. 2 is a view in the direction of arrow A in FIG. 1.

A gripping tool pertaining to one embodiment of the present invention will be explained in detail using figures. FIG. 1 is a side view with a part of gripping tool (100) pertaining to one embodiment of the present invention as a cross section, and FIG. 2 is a view in the direction of arrow A in FIG. 1. As can be seen from the figures, gripping tool (100) is constituted by main body (10), gripped part (20) and connecting part (30). Gripped part (20) and connecting part (30) are formed as a unit.

Figure 3:
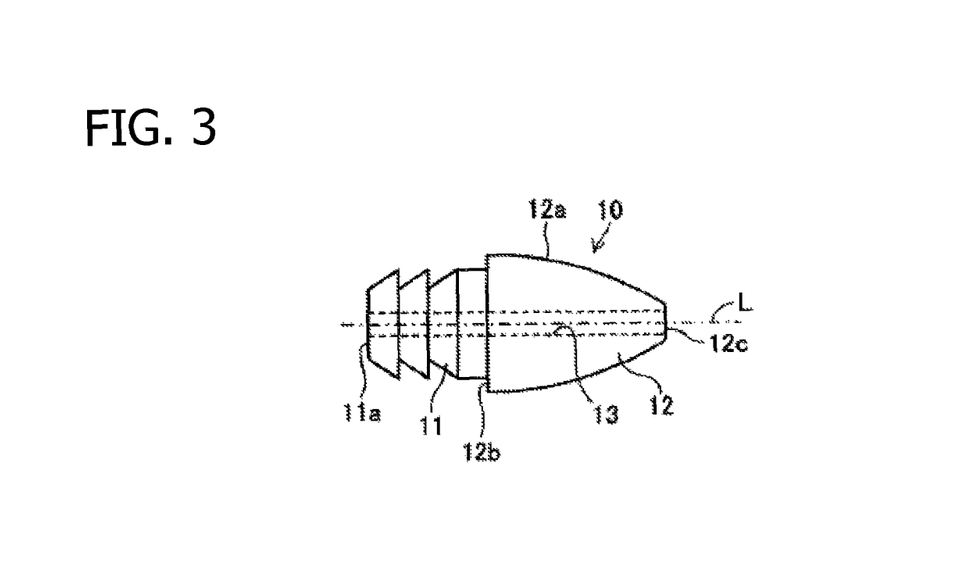
FIG. 3 is a side view of the main body pertaining to the embodiment of the present invention.

FIG. 3 is a side view showing only main body (10). Main body (10), as shown in FIG. 3, is formed symmetrically centered on axis (L) and is constituted by connection opening part (11) and guide part (12). Connection opening part (11) is the portion to which one end of the discharge tube is connected and has a known connection opening shape such that umbrella shapes are stacked in the direction of axis (L) as shown in the figure. Guide part (12) is formed connected to connection opening part (11) in the direction of axis (L) and has a slide surface (12a), the outer diameter of which decreases going from left to right in the figure, a large diameter end surface (12b) formed at the left end, in the figure, of slide surface (12a), and a small diameter end surface (12c) formed at the right end, in the figure, of slide surface (12a). Note that with this application example, the curved cross-sectional shape of slide surface (12a) with respect to the direction of axis (L) is at an oblique angle where the curvature increases (curvature radius decreases) going from the left to the right as can be seen from the figure, and it is formed into a truncated cone shape or a truncated bullet shape.

Connection opening part (11) is connected to large diameter end surface (12b) of guide part (12), and the diameter of large diameter end surface (12b) is larger than the diameter of connection opening part (11) at the connected portion. One end of the discharge tube touches the large diameter end surface (12b). A pass through channel (13) is also formed in main body (10) from one end surface (11a), which is the left end surface of connection opening part (11) in the figure, to small diameter end surface (12c) of guide part (12) in the direction of axis (L).

In this embodiment, guide part (12) is formed with polycarbonate (PC) resin, but it could also be formed with another hard plastic resin or a metal material. Slide surface (12a) is formed to give a smooth surface over which, when gripped by forceps, the forceps will slide and lose its grip on guide part (12).

Figure 4:
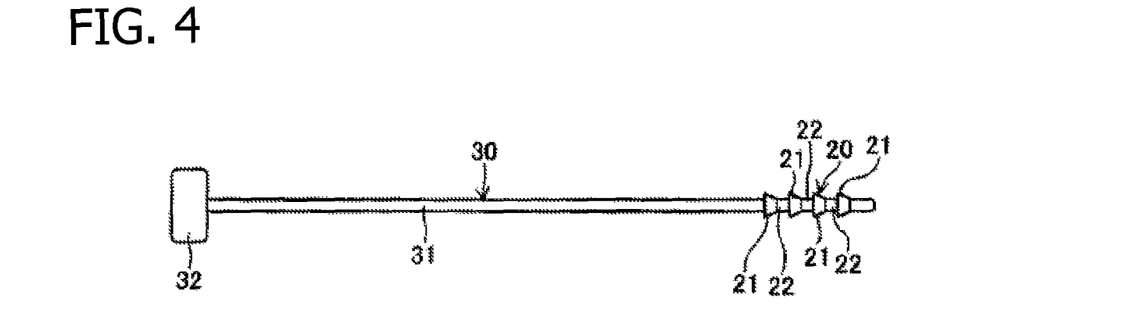
FIG. 4 is a side view of the gripped part and the connecting part pertaining to the embodiment of the present invention.

FIG. 4 is a cross section showing gripped part (20) and connecting part (30). Gripped part (20) is the portion gripped by forceps or the like and is where a plurality (in the figure, 4) of round truncated cone-shaped projecting parts (21), the diameter of which decreases going from left to right in the figure, are formed. A connecting part (22) that has a smaller diameter than the maximum diameter of projecting part (21) is also placed between adjacent projecting parts (21), and connecting parts (22) serve as spacers so that projecting parts (21) are disposed at a prescribed interval (interval the length of connecting part (22)). Note that for projecting parts (21) and connecting parts (22), the sets of adjacent projecting parts (21) and connecting parts (22) could also be formed as a unit, or they could be formed separately.

Connecting part (30) is formed connected to the back end (left end in the figure) of gripped part (20) and is constituted by a rod shaped part (31) and a stop (32). Rod shaped part (31) is formed in a long shape and its leading end (right end in the figure) is connected to gripped part (20). Rod shaped part (31) also has an outer diameter that is a smaller diameter than the inner diameter of pass through channel (13) formed in main body (10). The axial length of rod shaped part (31) is also longer than the length in the direction of axis (L) of pass through channel (13). Stop (32) is formed at the back end (left end in the figure) of rod shaped part (31), and with this embodiment, is formed in a rectangular solid shape with the corners rounded. Stop (32) outer diameter perpendicular to rod shaped part (31) is larger than the inner diameter of pass through channel (13).

Gripped part (20) and connecting part (30) in this embodiment are also formed as a unit with a soft resin, such as polyvinyl chloride resin, but they are not limited to this. For example, they can also be formed with polyethylene resin or another thermoplastic elastomer material. In particular, connecting part (30) could be any material, as long as it can be folded, curved or bent with slight force. For example, it could even be a cord in which fibers are joined. However, taking into account moldability when formed as a unit with gripped part (20), it should be formed with a soft resin material.

Figure 5:
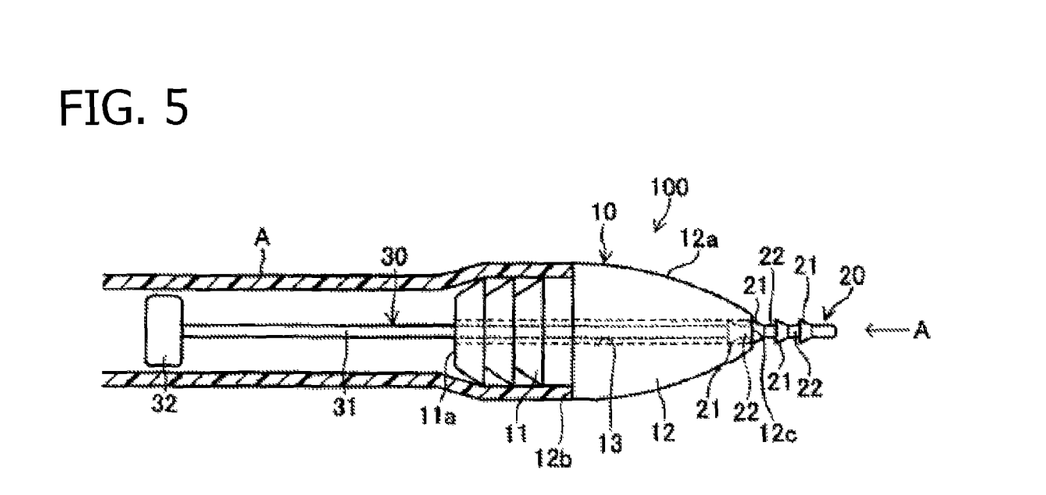
FIG. 5 is a side view in which a discharge tube is attached to a gripping tool pertaining to the embodiment of the present invention.

As shown in FIG. 1, a part of connecting part (30) and gripped part (20) are inserted into pass through channel (13) of main body (10). Gripped part (20) protrudes from small diameter end surface (12c) of main body (10) and rod shaped part (31) and stop (32) of connecting part (30) protrude from the one end surface (11a) of main body (10). The discharge tube is connected to gripping tool (100) through connection opening part (11). FIG. 5 shows discharge tube (A) attached to gripping tool (100). As shown in FIG. 5, one end of discharge tube (A) is spread by the portion of connection opening part (11) formed into an umbrella shape and is elastically affixed to the umbrella shaped portion, and its end surface touches large diameter end surface (12b) of guide part (12). In this state, connection opening part (11) is inserted into the discharge tube, and the one end surface (11a) of connection opening part (11) serves as an inner surface part facing the space inside the discharge tube. At the same time, slide surface (12a) and small diameter end surface (12c) of guide part (12) serve as the outer surface part exposed outside the discharge tube.

Therefore, as can be seen from FIG. 5, at connecting part (30), the portion of rod shaped part (31) protruding from the end surface (11a) of connection opening part (11) and stop (32) are disposed inside discharge tube (A). On the other hand, gripped part (20) protruding from small diameter end surface (12c) of guide part (12) is disposed in discharge tube (A) and gives a state where it appears from aforementioned small diameter end surface (12c).

Figure 6:
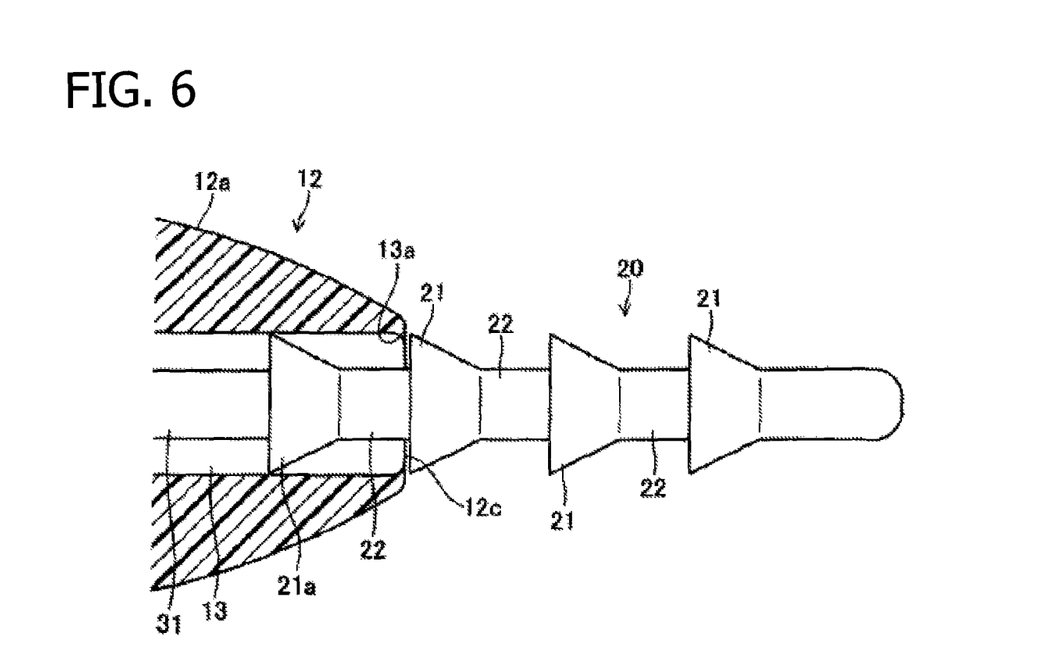
FIG. 6 is an enlarged view near the small diameter end of the guide part pertaining to the embodiment of the present invention.

FIG. 6 is an enlarged view near small diameter end surface (12c) of guide part (12). As shown in the figure, pass through channel (13) formed in main body (10) has a constricted part (13a) formed so that the diameter becomes slightly smaller from left to right in the figure near the open part toward small diameter end surface (12c). The opening diameter of constricted part (13a) at small diameter end surface (12c) is larger than the diameter of rod shaped part (31) and connecting part (22) of gripped part (20) and is slightly smaller than the maximum outer diameter of projecting parts (21) of gripped part (20). Also, as shown in the figure, projecting part (21a), which is the projecting part (21) most toward the back (left end in the figure), is disposed in pass through channel (13), and the other three project outside.

The opening diameter of pass through channel (13) at small diameter end surface (12c) is smaller than the maximum outer diameter of projecting parts (21), so projecting parts (21) protruding outside cannot enter pass through channel (13). Because of this, projecting parts (21) protruding outside become stops, and rod-shaped part (31) cannot move toward the left in the figures. On the other hand, when projecting part (21a) in pass through channel (13) tries to move toward the right in the figure to protrude from pass through channel (13), it must slip through the open part in small diameter end surface (12c) that has been deformed and is constricted. For this reason, it cannot easily protrude from pass through channel (13) due to the force of the resistance accompanying deformation, and movement by rod shaped part (31) toward the right in the figure is restricted by a prescribed force of resistance along with that movement.

By furnishing constricted part (13a) at the open end (small diameter end surface (12c)) of pass through channel (13) and because projecting part (21) is caught by small diameter end surface (12c), gripped part (20) and connecting part (30) can be affixed to main body (10). The component constituting gripped part (20) and connecting part (30) can be kept immobile relative to main body (10) when gripping tool (100) is transported, etc. Note that the state shown in FIG. 6 can be realized by pushing gripped part (20) from the open end toward end surface (11a) of pass through channel (13), pushing gripped part (20) out of small diameter end surface (12c) and stopping pushing in the state shown in FIG. 6.

In gripping tool (100) of this embodiment that is constituted as described above, first, discharge tube (A) is attached as shown in FIG. 5, and main body (10) is affixed to one end of discharge tube (A). Next, from the incision location incised during a surgical operation or the like, discharge tube (A) is inserted into the body with the side at which main body (10) is affixed (leading end) first. Then, discharge tube (A) is manipulated from the incision location by a technique so that the leading end of discharge tube (A) in the body approaches the open part in the aforementioned loculus. Then a forceps is inserted through the loculus and gripping tool (100) is gripped by the forceps.

Figure 7:
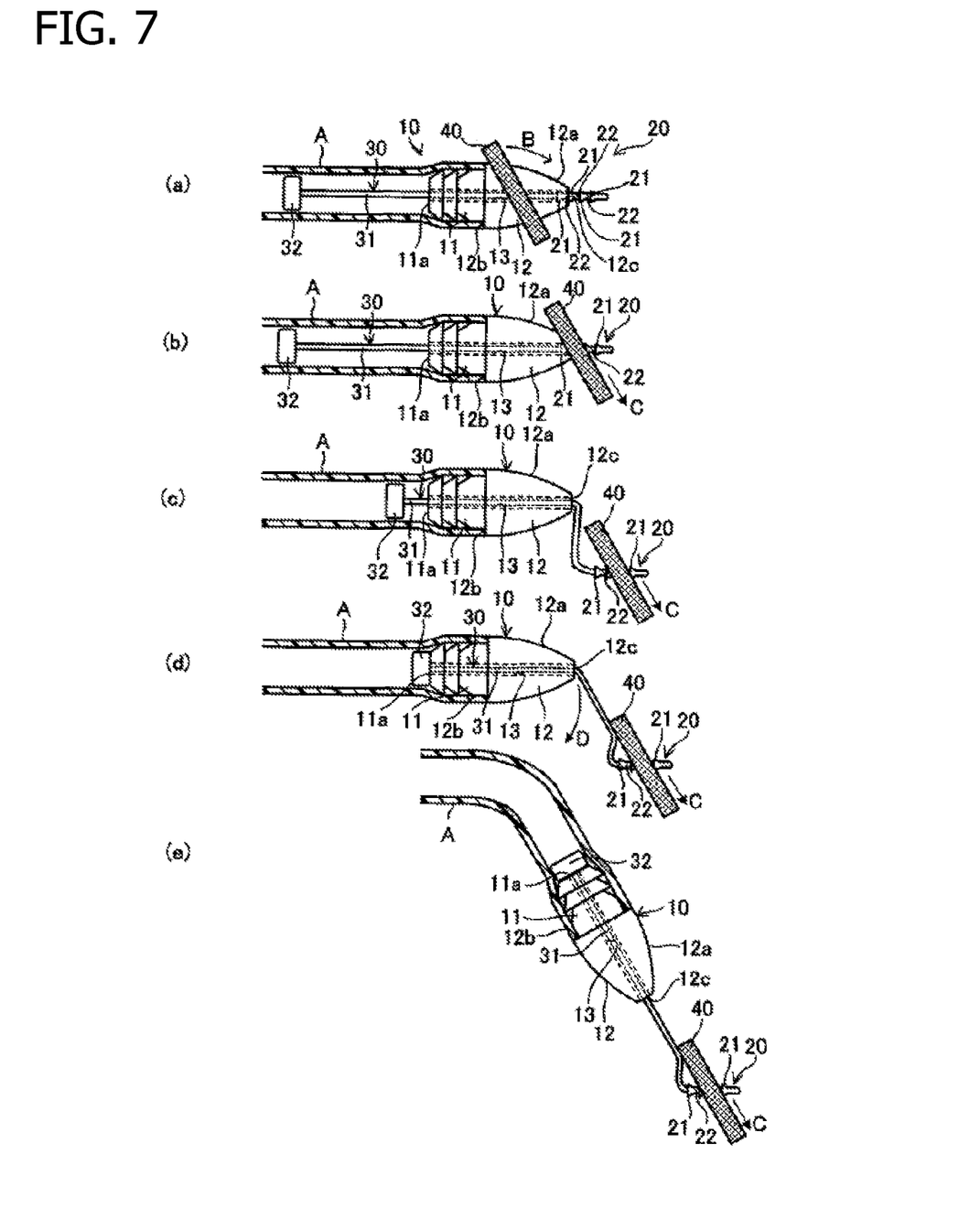

FIG. 7 shows the operation after gripping tool (100) is gripped by forceps (40) and forceps (40) is lifted to remove discharge tube (A) from the loculus. With this embodiment, gripping tool (100) is gripped in the manner shown in FIG. 7(a) by forceps (40) inserted through the loculus. Note that the operation to insert forceps (40) through the loculus to grip gripping tool (100) is a blind operation and the position in which gripping tool (100) is gripped by forceps (40) is often not known. Therefore, forceps (40) gripping gripping tool (100) in an oblique horizontal direction as shown in FIG. 7(a) sometimes occurs.

The gripping state shown in FIG. 7(a) is a state in which forceps (40), with respect to gripping tool (100), grips slide surface (12a) formed on guide part (12) of main body (10) in an oblique horizontal direction. Here, guide part (12) is formed with a hard plastic (polycarbonate resin), and slide part (12a) is formed smooth, so forceps (40) slides over slide surface (12a) by the gripping force it generates. Slide surface (12a) is also formed so that the outer diameter decreases toward small diameter end surface (12c) from large diameter end surface (12b), so forceps (40) slides as in arrow B in the figure from large diameter end surface (12b) toward small diameter end surface (12c). Then it slides down over main body (10) from small diameter end part (12c).

Pass through channel (13) is formed in small diameter end surface (12c) and gripped part (20) protrudes from this opening. Therefore, forceps (40) that has slid down from small diameter end surface (12c) will grip gripped part (20) by the tip that has slid down. This state is shown in FIG. 7(b). Even if forceps (40) grips main body (10), as an example, in this way, forceps (40) is guided to gripped part (20) by slide surface (12a), and ultimately forceps (40) grips gripped part (20). That is, guide part (12) has the function of guiding forceps (40) to gripped part (20). For this reason, gripped part (20) can be gripped reliably by forceps (40).

After the operator confirms that forceps (40) is gripping gripped part (20), forceps (40) is pulled out of the body. In this case, forceps (40) is pulled out of the loculus formed in the body, so it is pulled out along the portion in which the loculus is formed in the pull out direction. For example, assume that this direction is the direction of arrow C in FIG. 7(b). As shown in the figure, the direction of arrow C is different from the direction of discharge tube (A). When forceps (40) is pulled out in the direction of arrow C in the figure, gripped part (20) that is gripped in forceps (40) moves along with forceps (40). Connecting part (30) connected to gripped part (20) is also pulled out a prescribed distance from inside pass through channel (13) and discharge tube (A). Connecting part (30) is formed of a soft resin and can bend, so the portion that is pulled out bends as in FIG. 7(c).

When forceps (40) is pulled out farther, connecting part (30) is pulled out of discharge tube (A) and pass through channel (13) along with it. Soon stop (32) positioned at the end of connecting part (30) touches the one end surface (11a) formed in connection opening part (11) of main body (10) as shown in FIG. 7(d) and engages. Main body (10) and connecting part (30) are connected by this engaging, and gripped part (20) is connected to main body (10) by connecting part (30). Disengagement of connecting part (30) from main body (10) is also prevented by this touching, and further pulling out of rod shaped part (31) of connecting part (30) is prevented. For this reason, the part of rod shaped part (31) already pulled out is subjected to a tensile force from forceps (40) and is stretched tight, it bends at the portion protruding from main body (10) as shown in the figure, and the portion at the end is extended to follow the direction that forceps (40) is pulling. In such a state, a state in which a tensile force acts on rod shaped part (31) of connecting part (30) in the pull out direction is produced, and the tensile force is transmitted to main body (10) from connecting part (30). For this reason, main body (10) is pulled toward connecting part (30) in the pull out direction.

In this case, because main body (10) is subjected to an external force in the pull out direction from connecting part (30), its direction is changed to point toward the pull out direction by the moment of the external force. Here, since main body (10) is attached to one end of discharge tube (A), discharge tube (A) is also subjected to a rotation force in the direction of arrow D toward the pull out direction along with main body (10) due to the aforementioned moment, and the direction of discharge tube (A) is changed to the pull out direction by forceps (40) by using gripping tool (100) of the present invention. This state is shown in FIG. 7(e).

Therefore, when forceps (40) is pulled out through the loculus, gripping tool (100) and discharge tube (A) are pulled out through the loculus along with it, and since discharge tube (A) is guided in the pull out direction, no interference, such as catching on the edges of the loculus, occurs, and it can be pulled out rapidly. For this reason, discharge tube (A) can be guided out of a loculus with a small formation area.

With this embodiment as above, gripping tool (100) is constituted by a main body (10) that is affixed to one end of discharge tube (A), a gripped part (20) that is gripped by forceps (40), and a connecting part (30) that can bend and that also connects main body (10) and gripped part (20). Therefore, the direction of discharge tube (A) can be changed to the pull out direction by forceps (40) under the action described above, and when discharge tube (A) is guided from the body along with forceps (40), the sectional area for its passage through the loculus can be made sufficiently small. Thus, discharge tube (A) can be guided out reliably.

Also, in main body (10), a pass through channel (13) is formed that passes from one end surface (11a) that faces the inside of discharge tube (A) to small diameter end surface (12c) exposed outside discharge tube (A). Connecting part (30) is disposed through the inside of pass through channel (13) and is constituted so that one end is positioned inside discharge tube (A), and gripped part (20) is connected to the other end. At the aforementioned one end of connecting part (30), main body (10) and gripped part (20) are connected by engaging in main body (10) at one end surface (11a), and a stop (32) is attached to prevent disengagement of connecting part (30) from main body (10). Therefore, connecting part (30) can be housed inside pass through channel (13) of main body (10) and discharge tube (A), the space in which connecting part (30) is disposed can be reduced and gripping tool (100) can be constructed compactly.

When gripped part (20) is gripped and pulled out by forceps (40), connecting part (30) is pulled from the inside of pass through channel (13) and discharge tube (A) and is guided out of the discharge tube, so gripped part (20) and main body (10) can be separated by the distance that connecting part (30) is pulled out. For this reason, forceps (40) does not interfere with main body (10) in the process of being pulled out by forceps (40). Thus, obstruction of a change in direction of main body (10) and discharge tube (A) by the aforementioned interference can be prevented.

Multiple projecting parts (21) are also disposed at intervals on gripped part (20) with connecting parts (22) as spacers. For this reason, when forceps (40) grips gripped part (20), forceps (40) engages on any of projecting parts (21), and gripped part (20) can be gripped reliably. A slide surface (12a) is also formed on guide part (12) of main body (10), and when forceps (40) grips slide surface (12a), forceps (40) slides along slide surface (12a) and is guided to gripped part (20). Even if forceps (40) grips main body (10) via slide surface (12a), the constitution is such that it will ultimately arrive at gripped part (20) so that gripped part (20) can be gripped reliably.

Figure 8:
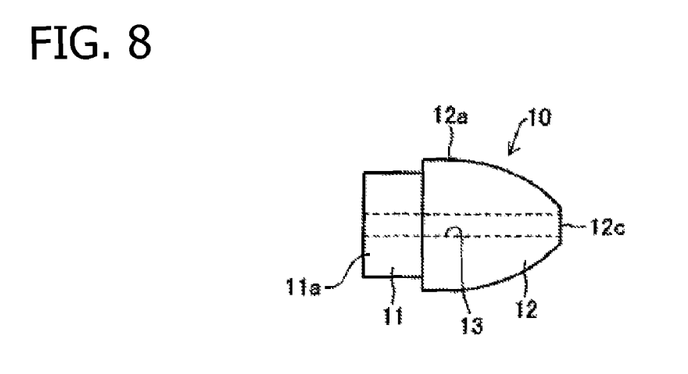
FIG. 8 is a side view showing another example of the main body in an embodiment of the present invention.
Figure 9:
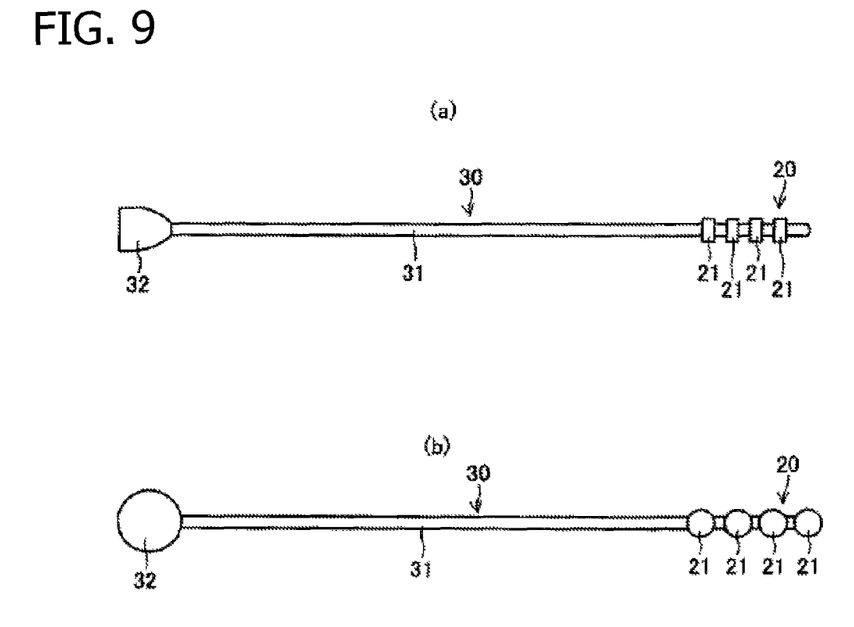

An embodiment of the present invention was explained above, but the present invention is not limited to the aforementioned embodiment. For example, with the aforementioned embodiment, the shape of main body (10) was explained based on a shape as shown in FIG. 3, but various changes are possible, such as providing connecting opening part (11) with a cylindrical shape and changing the slant angle of slide surface (12a) as shown in FIG. 8. In addition, the shape of gripped part (20), and particularly projecting parts (21), can have a spherical or rectangular solid shape as shown in FIG. 9. The shape of stop (32) can also be conical or spherical as shown in FIG. 9. Any of these changes is possible as long as the shape exhibits the function and effects accompanying the present invention.

One embodiment of the present invention was devised with the objective of providing a gripping tool that can be reliably gripped by a removal member such as forceps and that also makes it possible to pull the discharge tube out through a loculus with a small sectional area after gripping.

In order to accomplish the abovementioned objective, the features of the gripping tool pertaining to one embodiment of the present invention are that, in a gripping tool that is attached to one end of a flexible discharge tube for discharging fluids in the body outside the body and that is gripped by a removal member for pulling one end of the aforementioned discharge tube remaining in the body outside the body, there are provided a main body that is affixed to one end of the aforementioned discharge tube, a gripped part that is gripped by the aforementioned removal member, and a connecting part that can bend and that also connects the aforementioned main body and the aforementioned gripped part.

The abovementioned gripping tool of one embodiment of the present invention has a gripped part that is gripped by a removal member, such as a forceps, so it is gripped reliably by the removal member due to the gripped part. With the gripping tool of this embodiment, the connecting part that connects the main body and the gripped part is also constituted to be able to bend. Therefore, when the gripped part is pulled out by the removal member in a direction different from the direction of the one end of the discharge tube, the connecting part bends to follow the direction of pull out by the removal member. When pulled out farther in the direction of pull out in this state, a tensile force following the pull out direction acts on the connecting part, and this tension is transmitted to the main body from the connecting part. For this reason, the main body is pulled by the connecting part in the pull out direction.

In this case, because the main body receives an external force in the pull out direction from the connecting part, its direction is changed toward the pull out direction by the moment of the external force. Because the main body is attached to one end of the discharge tube, the directions of both the discharge tube and the main body are changed toward the pull out direction by the aforementioned moment. By using the gripping tool of the present invention, the direction of the discharge tube is changed toward the pull out direction by the removal tool in this way.

Therefore, when the removal member, such as forceps, is pulled out of the loculus, the gripping tool and the discharge tube are pulled out of the loculus accompanying the forceps, and because the discharge tube is guided following the pull out direction, the sectional area through which it passes through the loculus can be approximately equal to the discharge tube radial orientation sectional area. In this way, the sectional passage area for passage of the end of the discharge tube through the loculus can be made sufficiently small, so the discharge tube can be guided reliably through a loculus with a small sectional area.

In the present application, "can bend" means that it is possible for the connecting part to bend to follow the pull out direction due to the removal member. Therefore, it is assumed that this includes deformation caused by curving or the like, in addition to bending due to deformation such as buckling. Cases of bending structurally are also assumed to be included. Examples of constitutions for a connecting part that can bend include constitutions formed with a material that can bend, such as a cord like material, rubber material, or resin material. Examples where the connecting part can bend structurally include a constitution that connects the main body and the gripped part with a universal joint or a constitution where one end of the connecting part is connected inside the main body with a ball joint or the like and the other end is connected to the gripped part. For the direction that the connecting part can bend, it need only be able to bend in the pull out direction due to the removal member, but if it can bend in any direction, it can follow the pull-out direction whatever the direction.

In one embodiment of the present invention, the aforementioned main body may also be constituted by an inner surface part facing the inside of the aforementioned discharge tube and an outer surface part that is exposed on the outside of the aforementioned discharge tube, with a pass through channel formed to pass through from the aforementioned inner surface part to the aforementioned outer surface part, with the aforementioned connecting part disposed to pass through the aforementioned pass through channel, and with a stop attached to the aforementioned one end to prevent disengagement of the aforementioned connecting part from the aforementioned main body by engaging in the aforementioned main body from the aforementioned inner surface part.

With a constitution as described above, the connecting part can be housed in the pass through channel of the main body and the discharge tube, so the space in which the connecting part is disposed can be reduced and the gripping tool can be constructed compactly. Also, the connecting part can be constituted to be pulled out from inside the pass through channel and the discharge tube when the gripped part is gripped and pulled out by a removal member such as forceps. If the connecting part is constituted so that it can be pulled out in this way, the gripped part and the main body can be separated by the distance that the connecting part is pulled out. Thus, it can be constituted so that interference of the removal member, such as forceps, with the main body can be prevented, and so that the conversion of the direction of the main body and the discharge tube to the pull out direction will not be hindered by the aforementioned interference.

Multiple projecting parts may also be disposed at intervals on the aforementioned gripped part. If multiple projections are formed at intervals on the gripped part that is gripped by a removal member such as forceps, the gripped part can be gripped by the removal tool engaging in any of the projecting parts. For this reason, gripping with the removal tool will be easier. In this case, the aforementioned projecting parts could take a shape such as a spherical shape, a rectangular solid shape, or a circular truncated cone shape. Gripping with the removal member will be easier by using such shapes.

A slide surface can also be formed on the aforementioned main body to guide the aforementioned removal member to the aforementioned gripped part by sliding when the aforementioned removal member grips the aforementioned main body. In the event that the removal member should slide over the surface of the main body due to the slide surface when the removal member attempts to grip the main body, it will ultimately arrive at the gripped part and will grip the gripped part. For this reason, gripping using the gripped part can be accomplished more reliably.

As an example for realizing the aforementioned constitution, the aforementioned pass through channel is formed in the main body and a tapered slide surface where the tip is pointed is formed on the surface of the main body. The connecting part is also housed in the discharge tube and the pass through channel of the main body so that the gripped part will be positioned at the pointed portion of the aforementioned slide surface. In such a constitution, when the removal member grips the slide surface, the removal tool slides along the slide surface and is guided to the pointed portion of the slide surface. Because the gripped part is positioned at the pointed portion, the removal member grips the gripped part. When the removal member gripping the gripped part moves further in the pull out direction, the connecting part is pulled away from the discharge tube and the pass through passage, and the main body is pulled while bending. In this way, the directions of the main body and the discharge tube are changed.

Having described the embodiment(s) of the present invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A drainage tube assembly for at least partial insertion into a patient's body comprising:
   a drainage tube having an end for insertion into and removal from said body; and
   a gripping tool affixed to said drainage tube and arranged to be gripped with a removal member for pulling the end of said drainage tube remaining in a patient's body out of the body comprising:
     a main body configured for attachment to the distal end of said drainage tube and having a through channel;
     a gripping part configured to be gripped by said removal member, the gripping part including multiple projecting parts spaced longitudinally from each other; and
     a bendable connecting part that connects said main body and said gripping part, the connecting part disposed within said through channel and protruding proximally from said through channel;
     the main body, gripping part and connecting part of the tool each being separate from said drainage tube.

2. The drainage tube assembly according to claim 1, wherein:
   said main body has an inner surface part that is received in the inside of said drainage tube when the main body is attached to the drainage tube, the inner surface part being sized and shaped to elastically expand the drainage tube when received in the drainage tube;
   said main body has an outer surface part that is exposed to the outside of said drainage tube when the main body is attached to the drainage tube;
   said main body has a pass through channel passing from said inner surface part to said outer surface part; and
   said connecting part is disposed through the aforementioned pass through channel such that a first end thereof is adapted for positioning inside said drainage tube and said gripping part is connected to a second end thereof, said first end of the connecting part having a stop attached thereto to prevent disengagement of the said connecting part from said main body by engaging with said main body from said inner surface part when the gripping tool is used to remove the drainage tube from the body.

3. The drainage tube assembly according to claim 2, wherein the multiple projecting parts each have a maximum diameter greater than a maximum diameter of the pass through channel.

4. The drainage tube assembly according to claim 3, wherein said projecting parts have a form selected from the list of spherical, cylindrical and frusto-conical forms.

5. The drainage tube assembly according to claim 1, wherein a tapered slide surface is formed in said main body to direct said removal member to said gripping part when said removal member grips said main body.

6. A discharge tube assembly for at least partial insertion into a patient's body comprising:
   a discharge tube having an end for insertion into and removal from said body; and
   a gripping tool separate from the discharge tube, the gripping tool including a main body inserted in the end of the discharge tube, said main body having:
     a first end region inserted in said discharge tube end,
     a second end region protruding distally from said discharge tube end,
     a through channel connecting said first and second end regions,
     a connecting part disposed within said through channel and protruding proximally from said through channel away from the first end region; and
     a gripping element protruding distally away from said second end region including surface gripping protrusions spaced longitudinally from each other for gripping by a removal tool in a removal operation; and a stop for preventing pull-through of said connecting part through said through channel out of the second end region.

7. The discharge tube assembly according to claim 6 wherein said surface protrusions have a form selected from the list of spherical, cylindrical and frusto-conical forms, said surface protrusions being located outside the main body.

8. The discharge tube assembly according to claim 6 wherein said gripping element is slidably movable in said through channel.

9. The discharge tube assembly according to claim 6 wherein said gripping element is flexible.

10. The discharge tube assembly according to claim 6 wherein said gripping element is molded from a polymer resin.

11. A discharge tube assembly according to claim 6 in combination with said removal tool, said removal tool being formed to engage with the gripping protrusions of said gripping element.

12. A discharge tube assembly according to claim 6 wherein the first end region of the main body is sized larger than an internal diameter of the discharge tube in which it is received for attaching the main body to the discharge tube.

13. A discharge tube assembly according to claim 6 wherein the first end region of the main body is affixed to the discharge tube.

14. A gripping tool according to claim 1 wherein the main body is configured for affixing the main body in the drainage tube for conjoint movement therewith.

15. A discharge tube assembly according to claim 6 wherein the surface protrusions each have a maximum diameter greater than a maximum diameter of the through channel.

16. In combination, a drainage tube and a gripping tool for attachment to a distal end of a flexible drainage tube used for discharging fluids in the body, the gripping tool being arranged to be gripped with a removal member for pulling the end of said drainage tube remaining in a patient's body out of the body, the gripping tool comprising:

a main body configured for attachment to the distal end of said drainage tube, the main body having a narrow proximal portion and a wide distal portion, the narrow proximal portion configured for insertion into the distal end of the drainage tube to engage an inner surface of the drainage tube to hold the tool in the drainage tube, said body having a through channel;

a gripping part that is to be gripped by said removal member and includes multiple projecting parts spaced longitudinally from each other; and a connecting part that can bend and which connects said main body and said gripping part, the connecting part disposed within said through channel and protruding proximally from said through channel;

the main body, gripping part and connecting part of the tool each being separate from said drainage tube.

\* \* \* \* \*

UNITED STATES PATENT AND TRADEMARK OFFICE
CERTIFICATE OF CORRECTION

| | | |
|---|---|---|
| PATENT NO. | : 8,506,576 B2 | Page 1 of 1 |
| APPLICATION NO. | : 11/622825 | |
| DATED | : August 13, 2013 | |
| INVENTOR(S) | : Sutoh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this
Tenth Day of February, 2015

Michelle K. Lee
*Deputy Director of the United States Patent and Trademark Office*